United States Patent [19]
Trofast et al.

[11] Patent Number: 5,434,304
[45] Date of Patent: Jul. 18, 1995

[54] PROCESS FOR PREPARING FORMOTEROL AND RELATED COMPOUNDS

[75] Inventors: Jan W. Trofast, Lund; Edib Jakupovic, Nykvarn; Katarina L. Månsson, Älvsjö, all of Sweden

[73] Assignee: Aktiebolaget Astra, Sodertalje, Sweden

[21] Appl. No.: 309,167

[22] Filed: Sep. 20, 1994

Related U.S. Application Data

[63] Continuation of Ser. No. 175,691, Dec. 30, 1993, which is a continuation of Ser. No. 30,221, Mar. 23, 1993, abandoned.

[30] Foreign Application Priority Data

Sep. 26, 1990 [SE] Sweden ................................ 9003057

[51] Int. Cl.$^6$ ................. C07C 231/14; C07C 231/10; C07C 233/43

[52] U.S. Cl. ..................... 564/221; 564/219; 564/220; 560/21; 560/37; 568/583; 568/584; 568/585

[58] Field of Search ................. 564/221, 219, 220; 560/21, 37, 38; 568/583, 584, 585

[56] References Cited

U.S. PATENT DOCUMENTS

| | | | |
|---|---|---|---|
| 4,380,534 | 4/1983 | Fukui et al. | 424/498 |
| 4,975,466 | 12/1990 | Bottcher et al. | 514/630 |
| 5,079,008 | 1/1992 | Sinnreich et al. | 424/448 |
| 5,135,954 | 8/1992 | McDonald | 514/630 |

*Primary Examiner*—Arthur C. Prescott
*Attorney, Agent, or Firm*—White & Case

[57] ABSTRACT

The present invention is directed to a process for preparing formoterol and related compounds and derivatives thereof and their pharmacologically and pharmaceutically acceptable fumarate salts and/or solvates. The present invention is also directed to certain formoterol related compounds per se.

11 Claims, No Drawings

PROCESS FOR PREPARING FORMOTEROL AND RELATED COMPOUNDS

This application is a continuation of application Ser. No. 08/175,691, filed on Dec. 30, 1993, which is a continuation of application Ser. No. 08/030,221, filed on Mar. 23, 1993, abandoned.

Field of the invention

The present invention relates to an improved and simplified process for the preparation of formoterol and related compounds and derivatives thereof and their pharmacologically and pharmaceutically acceptable fumarate salts and/or solvates. The invention is also directed to new compounds as defined in claim 9. Formoterol is a longacting and highly selective bronchodilator. The $\beta_2$-adrenoceptor agonists taken by inhalation are the adminstration of choice in the symptometric therapy of obstructive airway disease.

BACKGROUND OF THE INVENTION

The administration by inhalation enables the dose to be delivered directly to the airways. By this route of adminstration, it is possible to give a small dose and thereby minimizing unwanted side-effects. The drawbacks of the current available bronchodilators are their relatively short duration of action. Studies with formoterol given by inhalation have shown its much longer duration than any other bronchodilators on the market. By using a compound with long duration it would be possible to avoid the nocturnal asthma, so often causing considerable anxiety and debility to the patients. Formoterol gives less nocturnal waking. Formoterol has been registered for oral adminstration in Japan since 1986.

Formoterol has two asymmetric carbon atoms in the molecule. It is used as the fumarate salt of one of the two possible pairs of enantiomers of 3-formamido-4-hydroxy-α-[N[1-methyl-2-(p-methoxyphenyl)ethyl-]aminomethyl]benzyl alcohol. Formoterol consists of the enantiomers, which have the RR+SS configuration.

Formoterol was first described in a Japanese patent application (Yamanouchi Pharmaceutical, Japan no 13121, priority 5 Feb. 1972, related priorities Japan no 39416 (19 Apr. 1972), 51013 (23 May 1972) and 52925 (27 May 1972)). The corresponding patent in Germany is DE 2 305 092.

DE 2 366 625 discloses some α-aminomethylbenzyl alcohol derivatives which are intermediates for preparing end products useful as bronchodilators. Example 3 therein refers to the preparation of 3-formamido-4-hydroxy-α-(N-benzyl-N-isopropylaminomethyl)benzylalcohol.

The hitherto published synthetic routes to formoterol involve a nucleophilic substitution reaction of an amine to a bromoketone according to:

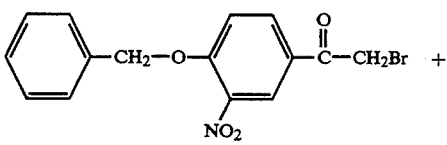

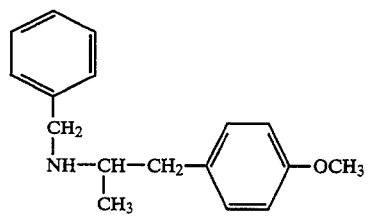

The reduction of the nitrogroup is accomplished by either Fe/HCl or Sn/HCl followed by formylation with a mixture of formic acid and acetic anhydride. The presence of acetic anhydride has shown to give some undesired acetylated products. The separation step of the two pairs of enantiomers are tedious and several recrystallizations are needed to obtain sufficient purity of the product.

The patent application J 50012-040 (priority date 31 May 1973) discloses a process where a substituted ketone is undergoing a reductive alkylation with the appropriate amine.

ES 2 005 492 (S. A. Lasa Laboratorios) describes a process for the synthesis of formoterol characterized by a coupling reaction between 3-formamido-4-benzyloxyphenyloxirane and the unprotected 2-(4-methoxyphenyl)-1 -methylethyl amine and is followed by tedious and troublesome steps (use of crown ethers, hydrofluoric acid, solvents like benzene and methylene chloride causing environmental and health problems, HCOOH/acetic anhydride etc.) to the final product.

The synthesis of formoterol and closely related compounds have also been reported in Chem. Pharm. Bull., 25(6), 1368-1377 (1977), where 3-nitro-4-benzyloxy-α-(N-substituted aminomethyl)benzyl alcohols are used as the keyintermediate. Use of Raney-nickel for the reduction of the nitro group has been rejected due to difficulties in obtaining pure products without a chromatographic step. However, the general procedure for the preparation of 3-amino-4-benzyloxy-α-(N-substituted aminomethyl)benzyl alcohols reported on page 1373 of said document involves a tedious and cumbersome column chromatographic step on silica gel using benzene-ethyl acetate as the eluent.

There is a strong desire of synthesizing formoterol fumarate (as dihydrate) by a simple procedure causing small environmental concerns e.g. by elimination of solvents like benzene.

BRIEF DESCRIPTION OF THE INVENTION

The present invention is directed to a process for preparing a compound of the general formula I

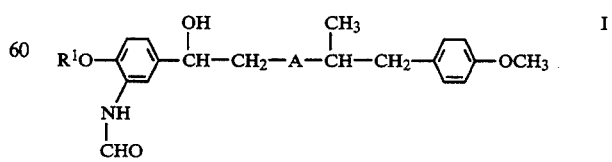

wherein $R^1$ is H or a straight or branched alkyl group having 1–5 carbon atoms,
A is either

wherein R is H or a straight or branched alkyl group having 1-5 carbon atoms and $R^2$ is H or a straight or branched alkyl group having 1-5 carbon atoms; or

wherein R is as defined above, or a pharmaceutically acceptable fumarate and/or solvate thereof, in the form of the pure racemates or the mixture of the four isomers, by a) reacting

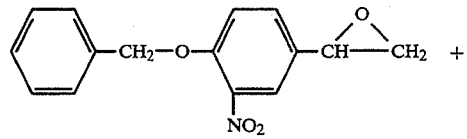

II

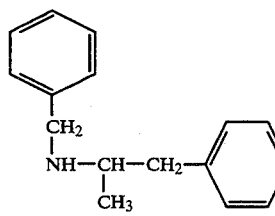

III to give compound IV

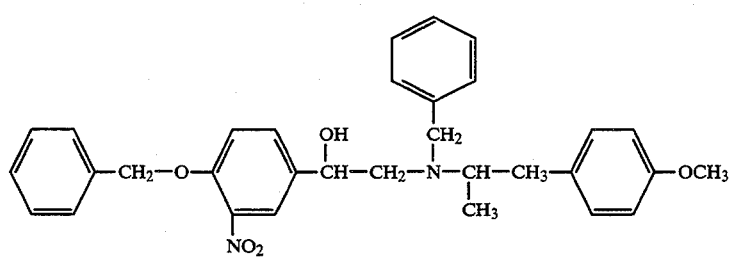

b) reducing and formylating compound IV to give compound V

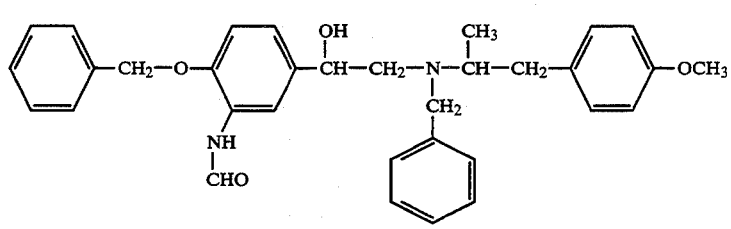

c) forming the fumarate of compound V and resolving the racemates by crystallization, d) extracting the base of the desired racemate of compound V, e) hydrogenolyzing of the protecting benzyl groups of said base of compound V to obtain compound I wherein A is

and $R^1$ is H, and optionally f) forming a fumarate and/or solvate of compound I, and optionally g) when A is either

wherein R is H or a straight or branched alkyl group having 1-5 carbon atoms and $R^2$ is H or a straight or branched alkyl group having 1-5 carbon atoms; or

wherein R is a straight or branched alkyl group having 1-5 carbon atoms, and $R^1$ is as defined above, alkylating the compound obtained in step e) or f).

Another aspect of the present invention refers to a new compound of the general formula I

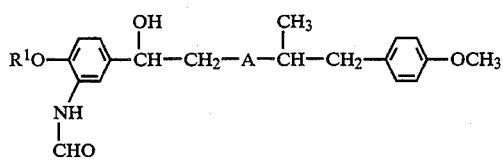

IV wherein R[1] is H or a straight or branched alkyl group having 1-5 carbon atoms, A is either

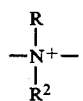

wherein R is a straight or branched alkyl group having 1-5 carbon atoms and R[2] is H or a straight or branched alkyl group having 1-5 carbon atoms; or

wherein R is as defined above, or a pharmaceutically acceptable fumarate and/or solvate thereof, in the form of the pure racemates or the mixture of the four isomers.

DETAILED DESCRIPTION OF THE INVENTION

The starting material 4-benzyloxy-3-nitro-styreneoxide (4-benzyloxy-3-nitro-phenyloxirane) (II) is prepared according to the method described in J. Med. Chem. 17, 49 (1974) by C. Kaiser et al.

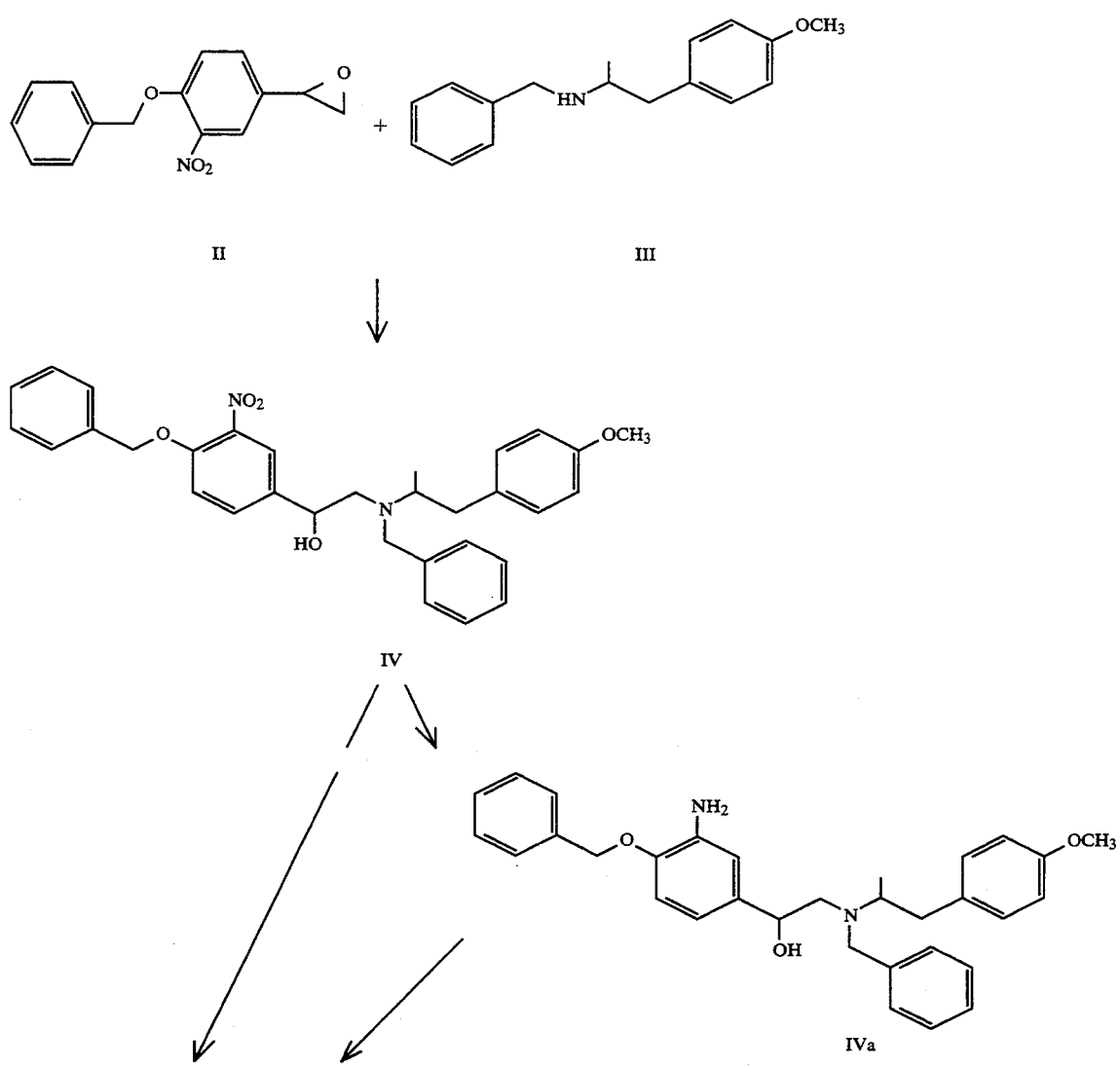

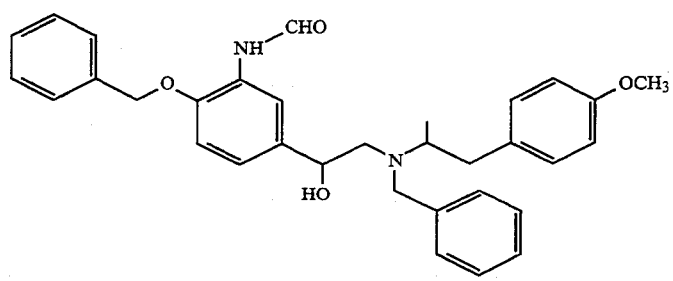

V

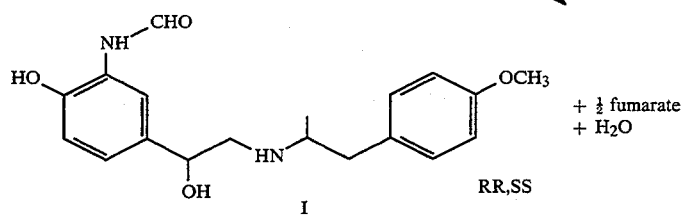

+ ½ fumarate
+ H₂O

I

According to the present invention formoterol, i.e. the compound of formula I wherein R and R¹ are hydrogen, is prepared by a) reacting

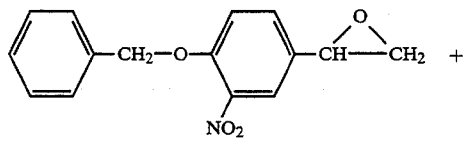

II

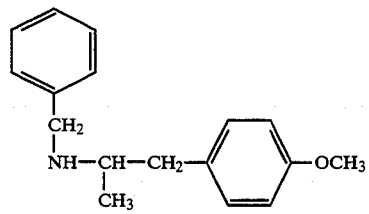

III in the presence of a solvent such as lower alcohols at reflux temperatures or in the absence of a solvent at temperatures preferably at 80°-120° C., to give compound IV b) reducing and formylating compound IV to give compound V in either a one step reaction with e.g. Raney-nickel/formic acid or in a two step reaction (catalytic reduction of the nitro group, e.g. over platinum metals in a polar solvent, such as lower alcohols and/or esters, preferably PtO₂ in methanol or more preferably Pt/C in ethyl acetate, to give compound IVa, followed by formylation, e.g. in a 6–10 fold excess of formic acid). The formylation step is preferably performed at a temperature of 20°-90° C. during 1-24 hrs. The mixture of the two racemates of V (RR+SS and RS+SR resp.) are thereafter separated by c) transforming the amine base into its fumarate salt for separation by fractional crystallization in a solvent system comprising ethyl acetate, isopropyl acetate and/or methyl isobutylketone. A very efficient system is based upon a solvent system which also comprises small amounts (preferably less than 15 %) of solvents more polar than the solvents just mentioned, such as dimethylformamide (DMF), dimethylsulfoxide (DMSO) and/or methanol. A preferred solvent system comprises ethyl acetate and a small amount of dimethylformamide, dimethylsulfoxide or methanol. The presence of a solvent like DMF is very important in order to increase the solubility and thereby improve the purity of the desired diastereomer.

Step e) is a common hydrogenolysis of the protecting benzyl groups of the amine base V, performed in a

IV

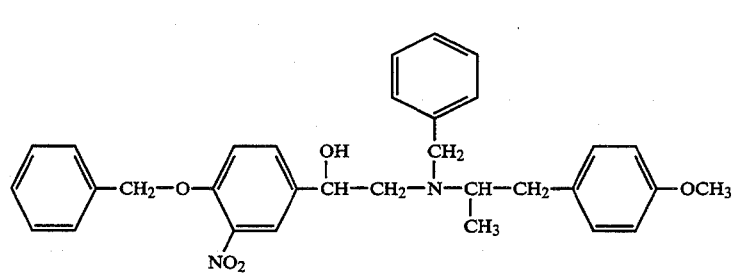

traditional manner with platinum, palladium, and nickel catalysts in a polar solvent, such as ethanol, isopropanol or ethylacetate or a mixture of said solvents, at normal, or higher temperature and pressure. A simple crystallization of the formoterol base by means of isopropanol or preferably by means of a isopropanol/water mixture may be carried out in connection with this step as a work up procedure. Said crystallizion should be carried out at a temperature as low as possible (e.g. <45° C.).

The formoterol may thereafter in step f) be transformed into its fumarate salt and/or solvate and crystalized in a polar solvent (isopropanol, ethanol and the like) containing some water (2–25%, preferably 20 %) in order to obtain suitable solide state properties of the compound (hydrate) for the micronization procedure. The compounds usually exist as solvates (hydrates) giving the possibility of different crystal arrangements (polymorphism).

The solvents may or may not be completely evaporated in each step in the process. It is preferred by technical reasons not to evaporate the solvents.

In case R in formula I is a straight or branched alkyl group having 1–5 carbon atoms, such as methyl, ethyl, propyl, iso-propyl, a further step g) is necessary, wherein the compound obtained in step e) or step f) is alkylated in a conventional manner, such as by nucleophilic substitution with alkyl halides or by reductive alkylation.

R in the definition of compound I is preferably hydrogen or a straight alkyl group of 1 to 3 carbon atoms.

EXAMPLES

The invention is further illustrated but not limited by the following examples.

Test methods

The purity of the synthesized compounds has been determined on a HPLC (high performance liquid chromatography) system with UV detection using a Li-Chrosphere RP Select B 5 μm (125×4 mm) column under the following conditions:

System A:
 Mobile phase: $CH_3CN$:phosphate buffer pH 4.95 (55:45)
 Detect-ion wavelength: 280 nm
 Flow rate: 1.0 ml/min
 Retention time (min): II 4.8; III 1.9; IV 15 (RR,SS) 17 (RS,SR); IVa 6.7; V 5.5

System B:
 Mobile phase: $CH_3CN$:ethanol:phosphate buffer pH 4.95 (24:16:60)
 Detection wavelength: 280 (220) nm
 Flow rate: 1.0 ml/min
 Retention time (min): V 40 (RR,SS) 48 (RS,SR)

System C:
 Mobile phase: $CH_3CN$:ethanol: 0.1M $NH_4OAc$ in 0.1M HOAc (11:11:78)
 Detection wavelength: 280 nm
 Flow rate: 0.8 ml/min
 Retention time (min): I 8.7

The reactions have continously been followed by HPLC and the given data for yield, purity are taken directly from the chromatogram unless otherwise stated.

Preparation

Synthesis of IV. (step a)
 4-Benzyloxy-3-nitro-styrenoxide (II 0.5 mole, 135.8 g) and p-methoxyphenyl-2-benzylaminopropane (III, 0.55 mole 140.5 g) were stirred under nitrogen atmosphere at 90° C. for 69 hours (no solvent). The dark syrup (267.0 g) consisted of 94% of compound IV with a diastereomer ratio of 43:57 (System A).

Synthesis of V. (step b)
 Method-A (two steps). The dark syrup (IV, 133.5 g) in methanol (1.5 l) was hydrogenated over 1.5 g $PtO_2$ $xH_2O$ at a pressure of 2–4 bar for 3 hours. Compound IVa with a purity of 91% was obtained (System A). Filtration and evaporation of the solvent followed by addition of a seven fold excess of formic acid gave after standing for 24 hours at 20° C. compound V with a purity of 87% V (System A) after evaporation. The reaction mixture was used without further purification.

An alternative of Synthesis of IV and V
 4-Benzyloxy-3-nitro-styreneoxide(II, 164 mole, 44.5 kg) and p-methoxyphenyl-2-benzylaminopropane (III, 179 mole, 45.8 kg) were stirred under nitrogen atmosphere at 90° C. for 65 hours (no solvent). To the dark syrup dissolved in ethyl acetate (350 l) was added Pt/C (5.6 kg). Hydrogenation with hydrogen gas gave after evaporation of the solvent an oily solid of V with 91.3 % purity. The product was used without further purification.

Method B (one step)
 The dark syrup (IV, 5.0 g), Raney nickel (5 g) and 75% (v/v) aqueous formic acid (50 ml) were refluxed for 1 hr. The mixture was filtered, and the filtrate and washings diluted with water and extraxted with chloroform. The extracts were washed with saturated sodium hydrogen carbonate, water and dried ($Na_2SO_4$). The oily residue was chromatographed on a silica column using petroleum ether (40°–60° C.)/ethyl acetate (7.5:6) as eluent giving pure compound V (1.8 g).

Separation of the diastereomers (step c)
 To fumaric acid (0.62 mole, 72.5 g) dissolved in methanol (2 l) the reaction mixture consisting of compound V (about 1.25 mole) in formic acid was added. After evaporation of the solvents at 50° C. the brown syrup was dissolved in ethyl acetate (7.5 l) while heating. The light brown crystals of compound V fumarate formed during cooling were filtered, washed with ethyl acetate (1l) and dried in vacuum at 40° C. for 20 hours. The product (1.12 mole, 654.7 g) had a diastereomer ratio of 84:16 (System B). 1.10 mole (644.7 g) of compound V fumarate in ethyl acetate (7.5 l) was heated to reflux, DMF (750 ml) was added and the clear solution was allowed to stand for 4 days at room temperature. The light brown crystals formed, were washed with ethyl acetate (1.5 l) and dried in vacuum at 40° C. for 4 hours giving a diastereomer ratio of 98.5:1.5. By repeating the recrystallization procedure, a racemic purity of compound V of almost 100% was obtained in good yield (System B).

Synthesis of I.

Step d
 The protected (N,O-dibenzylated) formoterol base (V) was obtained by an extraction procedure (ethyl acetate (2 l)/ammonia, 2M (1.5 l)) from compound V fumarate (0.28 mole, 164.1 g).

Step e
 Hydrogenolysis of compound V (0.28 mole) in ethanol (2.5 l) with 5% Pd/C (16.0 g) at 45 psi over night gave the formoterol base (0.23 mole, 78 g (82%); purity 99.2%) after filtration and evaporation of the solvent. Recrystallization in isopropanol (1.1 l) increased the purity to 99.8%. An alternative procedure for recrystallization giving even better purity (>99.9%) involves the use of a mixture of isopropanol/water (e.g. 85:15)

and keeping the temperature as low as possible (e.g. <45° C.).

Step f.

To formoterol base (0.176 mole, 60.6 g) in isopropanol (960 ml) and water (200 ml) fumaric acid (0.088 mole, 10.21 g) was added. A clear solution was obtained after heating. After standing at room temperature the crystals were filtered, washed with isopropanol (2×50 ml) and dried in vacuum at 45° C. for two days. The formoterol fumerate dihydrate formed (0.17 mole, 69.7 g) had a purity of 99.2% and an diastereomeric purity of 99.8% (System C). ¹H-NMR (Varian VXR 300, deuterated dimethylsulfoxide, chemical shift in ppm): —CH(CH₃)—0.99 (3H, doublet); —CH(CH₃)—3.0-3.1 (1H, multiplet); —CH(OH)—4.60-4.65 (1H, multiplet); —CH₂—NH—2.75-2.9 (2H, multiplet); —CH(CH₃)—CH₂—2.44-2.5, 2.75-2.9 (2H, two multiplets); —OCH₃ 3.73 (3H, singlet); —CHO 9.61 (1H, doublet); —NH—CHO 8.29 (1H, doublet).; —CH=C—6.49 (1H, singlet). In the thermospray mass spectrum the assignment fragments are m/z 345 (MH+, 100%); 327 (MH+ —H₂O, 27%); 166 (C₁OH₁ 5N₃O+7.2%), which confirm the structure.

Synthesis of N-[2-(3-formamido-4-hydroxy-phenyl)-2-hydroxy-ethyl]-N,N-dimethyl-N-(p-methoxy-α-methyl-phenylethyl)ammonium fumarate A mixture of formoterol fumarate (500 mg), sodium carbonate (200 mg), methyl iodide (5 ml) and acetonitrile (50 ml) was stirred over night at room temperature. Filtration and evaporation of the filtrate gave an oily solid which was washed with chloroform to give 341 mg (66%) of the crude N-[2-(3-formamido-4-hydroxy-phenyl)-2-hydroxy-ethyl]-N,N-dimethyl-N-(p-methoxy-α-methylphenylethyl)ammonium fumarate. Recrytallization from 95% ethanol gave a purity of 98.6% (HPLC system: Licrosphere RP Select B, 5 μm, 129×4 mm, 214 nm, gradient elution from acetonitrile/-phosphate buffer (50 mM, pH 3) 16/84 to acetonitrile/-phosphate buffer (70/30), 1 ml/min). ¹H-NMR: —CH(CH₃)—1.17 (3H, doublet); N—CH₃ 3.2 (3H, singlet); N—CH₃ 3.3 (3H, singlet); —CH(CH₃) 4.0 (1H, multiplet); —CH(OH) 5.1-5.2 (1H, broad doublet); —CH(OH) 6.1 (broad singlet); —OCH₃ 3.76 (3H, singlet); CHO 8.31 (1H, singlet); —NHCHO 9.6 (1H, singlet); —CH=CH—6.9 (1H, singlet). The electrospray mass spectrum shows the molecular peak at m/z 373 which is in accordance with the proposed structure.

The new process according to the invention, which differs from known procedures for the preparation of formoterol fumarate and its derivatives in the following major ways 1. The use of an epoxide as a starting material
2. Reduction and formylation of the nitro group
3. The optional use of a cosolvent in the separation of the racemates.

The new process is easier to use and gives an end product with a higher purity than the same compounds prepared according to earlier known processes.

We claim:

1. A process for preparing a compound of the formula I

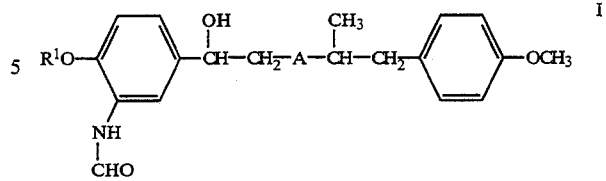

wherein R¹ is H or a straight or branched alkyl group having 1-5 carbon atoms, A is either

wherein R is a straight or branched alkyl group having 1-5 carbon atoms and R² is H or a straight or branched alkyl group having 1-5 carbon atoms; or

wherein R is as defined above, in the form of a pure racemate, which comprises the steps of a) reacting

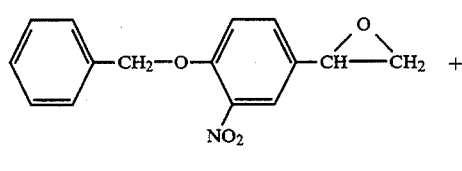

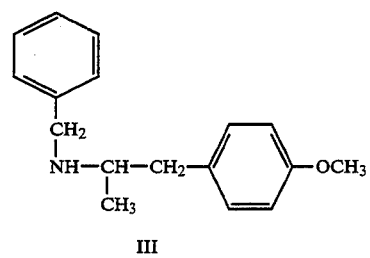

to give compound IV

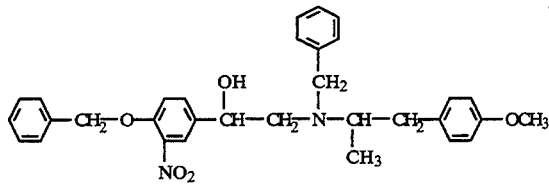

b) reducing and formylating compound IV to give compound V

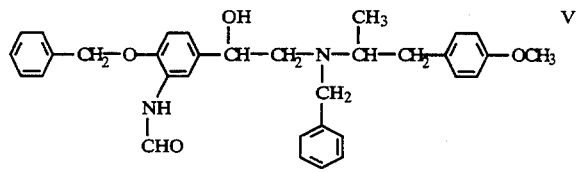

c) forming the fumarate of compound V and separating the racemates by crystallization,
d) extracting the base of the desired racemate of compound V,
e) hydrogenolyzing of the protecting benzyl groups of said base of compound V and
f) alkylating the compound obtained.

2. A compound of the formula I

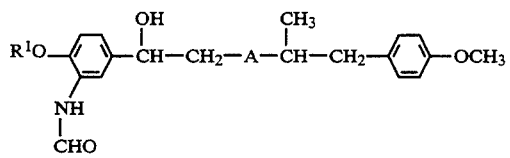

or a pharmaceutically acceptable fumarate and/or solvate thereof, in the form of the pure racemates or a mixture of the four isomers, wherein $R^1$ is H or a straight or branched alkyl group having 1-5 carbon atoms, A is either

wherein R is a straight or branched alkyl group having 1-5 carbon atoms and $R^2$ is H or a straight or branched alkyl group having 1-5 carbon atoms; or

wherein R is as defined above.

3. A process for preparing a compound of the formula I

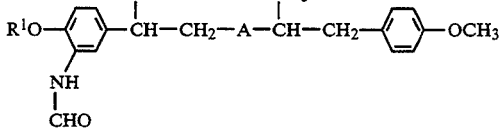

wherein A is

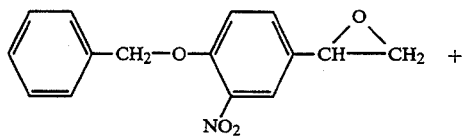

and $R^1$ is H, in the form of a pure racemate, which comprises the steps of
a) reacting

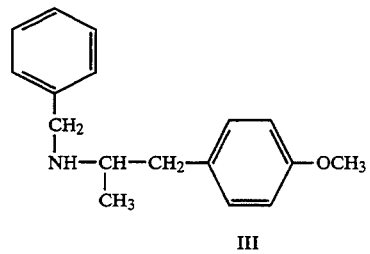

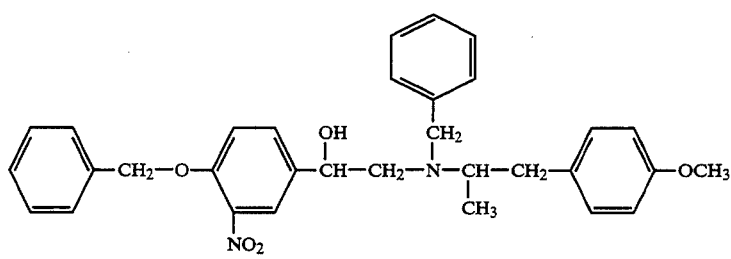

to give compound IV b) reducing and formylating compound IV to give compound V

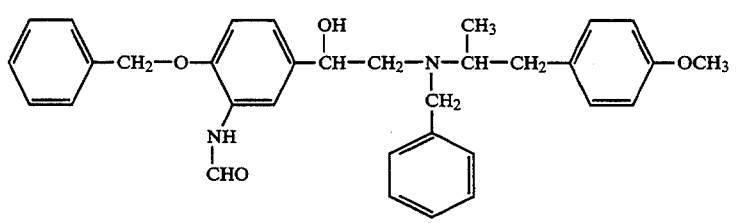

c) forming the fumarate of compound V and separating the racemates by crystallization, d) extracting the base of the desired racemate of compound V, and e) hydrogenolyzing the protecting benzyl groups of said base of compound V.

4. The process of claim 1, which further comprises, prior to step f), the step of forming a pharmaceutically acceptable fumarate and/or solvate of the compound resulting from step e).

5. The process of claim 3, which further comprises the step of forming a pharmaceutically acceptable fumarate and/or solvate of the compound resulting from step e).

6. The process according to claim 1, 3, 4 or 5, wherein step a) is carried out in the presence of a solvent, such as a lower alcohol, at reflux temperature or in the absence of a solvent at a temperature in the range of 80°–120° C.

7. The process according to any one of claims 1, 3, 4 and 5, wherein step b) is a one-step reaction with Raney-nickel/formic acid or a two-step reaction comprising catalytic reduction of the nitro group followed by formulation in an excess of formic acid.

8. The process according to any one of claims 1, 3, 4, and 5, wherein the separating of the racemates by crystallization in step c) is carried out in a solvent system comprising ethyl acetate, isopropyl acetate and/or methyl isobutylketone.

9. The process according to claim 8, wherein the solvent system further comprises small amounts of solvents more polar than the solvents defined in claim 8, such as dimethylformamide, dimethylsulfoxide and/or methanol.

10. The process according to claim 9, wherein the amount of the more polar solvent is less than 15%.

11. The process according to claims 1 or 4, wherein $R^2$ is a straight or branched alkyl group having 1–5 carbon atoms.

* * * * *